(12) United States Patent
Xu et al.

(10) Patent No.: US 7,465,845 B2
(45) Date of Patent: *Dec. 16, 2008

(54) INCREASING ETHYLENE AND/OR PROPYLENE PRODUCTION IN AN OXYGENATE TO OLEFINS REACTION SYSTEMS

(75) Inventors: Teng Xu, Houston, TX (US); Stephen Neil Vaughn, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 632 days.

This patent is subject to a terminal disclaimer.

(21) Appl. No.: 11/060,519

(22) Filed: Feb. 17, 2005

(65) Prior Publication Data

US 2006/0135834 A1    Jun. 22, 2006

Related U.S. Application Data

(60) Provisional application No. 60/638,838, filed on Dec. 22, 2004.

(51) Int. Cl.
*C07C 1/00* (2006.01)

(52) U.S. Cl. .................... 585/640; 585/638; 585/639

(58) Field of Classification Search .......... 585/638–640
See application file for complete search history.

(56) References Cited

U.S. PATENT DOCUMENTS

| | | | |
|---|---|---|---|
| 4,062,905 A | 12/1977 | Chang et al. ............ 260/682 |
| 4,079,095 A | 3/1978 | Givens et al. ............ 260/682 |
| 4,310,440 A | 1/1982 | Wilson et al. ............ 252/435 |
| 4,440,871 A | 4/1984 | Lok et al. ............ 502/214 |
| 4,499,327 A | 2/1985 | Kaiser ............ 585/640 |
| 4,542,252 A * | 9/1985 | Graziani et al. ............ 585/640 |
| 4,638,106 A | 1/1987 | Pieters et al. |
| 4,677,242 A | 6/1987 | Kaiser ............ 585/638 |
| 4,677,243 A | 6/1987 | Kaiser ............ 585/638 |
| 4,873,390 A | 10/1989 | Lewis et al. ............ 585/638 |
| 5,095,163 A | 3/1992 | Barger ............ 585/640 |
| 5,367,100 A | 11/1994 | Gongwei et al. ............ 585/640 |
| 5,714,662 A | 2/1998 | Vora et al. ............ 585/640 |
| 6,046,372 A | 4/2000 | Brown et al. ............ 585/640 |
| 6,051,746 A | 4/2000 | Sun et al. ............ 585/639 |
| 6,137,022 A | 10/2000 | Kuechler et al. ............ 585/638 |
| 6,166,282 A | 12/2000 | Miller ............ 585/638 |
| 6,436,869 B1 | 8/2002 | Searle et al. ............ 502/214 |
| 6,437,208 B1 | 8/2002 | Kuechler et al. ............ 585/640 |
| 6,613,950 B1 * | 9/2003 | Vaughn et al. ............ 585/639 |
| 7,396,971 B2 * | 7/2008 | Smith et al. ............ 585/640 |

FOREIGN PATENT DOCUMENTS

| | | |
|---|---|---|
| EP | 0 448 000 | 9/1998 |
| EP | 0 882 692 | 12/1998 |
| GB | 2171718 A * | 9/1986 |
| WO | WO 01/62382 | 8/2001 |
| WO | WO 2004/018089 | 3/2004 |

* cited by examiner

*Primary Examiner*—Glenn Caldarola
*Assistant Examiner*—In Suk Bullock (57) ABSTRACT

This invention is directed to a process for converting oxygenate to olefin product at an increased prime olefin selectivity (i.e., increased ethylene and/or propylene content) compared to conventional systems. The increase in ethylene and/or propylene content of the produced olefin product is accomplished using a reaction system that has at least two stages. Any number of stages can used in the entire process, as long as there are at least two stages in series and the temperature of any subsequent stage in series is lower than that of the preceding stage.

20 Claims, 2 Drawing Sheets

INCREASING ETHYLENE AND/OR PROPYLENE PRODUCTION IN AN OXYGENATE TO OLEFINS REACTION SYSTEMS

CROSS REFERENCE TO RELATED APPLICATIONS

This application claims the benefit of Provisional Application No. 60/638,838 filed Dec. 22, 2004, the disclosure of which is fully incorporated herein by reference.

FIELD OF THE INVENTION

This invention relates to methods for increasing ethylene and/or propylene production in an oxygenate to olefins reaction system. In particular, this invention relates to increasing ethylene and/or propylene production in an olefins reaction system by controlling the temperature of the reaction process, controlling the amount of coke on the molecular sieve, and/or applying a pretreatment composition to the molecular sieve.

BACKGROUND OF THE INVENTION

Oxygenates such as methanol are used as a feedstock for a variety of chemical manufacturing processes. An example of one process is the conversion of methanol or dimethyl ether to olefin products, particularly products containing the olefins ethylene and propylene. The olefins produced from the conversion process are of suitable quality to be used in polymer manufacturing processes. Of a commercial concern in the oxygenate conversion process, however, is whether sufficient quantities of light olefins (i.e., ethylene and propylene) can be produced.

Conventional molecular sieves used in converting methanol or other types of oxygenates to olefins are zeolites and various metalloaluminophosphates. For example, U.S. Pat. No. 5,367,100 describes the use of the zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; and U.S. Pat. No. 4,310,440 describes producing light olefin(s) from an alcohol using a crystalline aluminophosphate, often designated $AlPO_4$.

Other catalysts that be used to convert oxygenates to olefin(s) are silicoaluminophosphate (SAPO) molecular sieves. The SAPO molecular sieves contain a three-dimensional microporous crystalline framework structure of $[SiO_4]$, $[AlO_4]$ and $[PO_4]$ corner sharing tetrahedral units. SAPO synthesis is described in U.S. Pat. No. 4,440,871, which is herein fully incorporated by reference. SAPO molecular sieves are generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, are disclosed in U.S. Pat. Nos. 4,499,327, 4,677,242, 4,677,243, 4,873,390, 5,095,163, 5,714,662 and 6,166,282, all of which are herein fully incorporated by reference.

Typically, molecular sieves are formed into molecular sieve catalyst compositions (generally referred to as formulated catalysts) to improve their durability in commercial conversion processes. These formulated catalyst compositions are conventionally formed by combining molecular sieve, and one or more matrix materials, with a binder. The binder acts to hold the matrix material to the molecular sieve.

U.S. Pat. No. 4,677,242 (Kaiser) describes the use of a SAPO molecular sieve catalyst for converting various oxygenates, such as methanol, to olefins. According to the patent, the SAPO catalyst is an extremely efficient catalyst for the conversion of oxygenates to light olefin products when the feed is converted in the presence of a diluent. The diluent used has an average kinetic diameter larger than the pores of the SAPO molecular sieve. The selected SAPO molecular sieves have pores that an average diameter characterized such that the adsorption capacity (as measured by the standard McBain-Bakr gravimetric adsorption method using given adsorbate molecules) shows adsorption of oxygen (average kinetic diameter of about 3.36 angstroms) and negligible adsorption of isobutane (average kinetic diameter of about 5.0 angstroms).

U.S. Pat. No. 6,046,372 (Brown et al.) discloses another method of converting methanol to light olefins. The method incorporates the use of medium pore zeolite molecular sieves, particularly medium pore ZSM type zeolites, in converting methanol and/or dimethyl ether to light olefin. Light olefin production is aided by the use of an aromatic compound as a co-feed. The aromatic compound has a critical diameter less than the pore size of the catalyst, and is capable of alkylation by the methanol and/or dimethyl ether. Ethylene product selectivity is believed to be derived from the back-cracking of ethyl-aromatic intermediates. The formation of the ethyl-aromatic intermediates is believed to be facilitated by a mechanism in which the aromatic compound effectively acts as a catalyst in the conversion of two molecules of methanol to one molecule of ethylene.

U.S. Pat. No. 6,051,746 (Sun et al.) also describes a method for increasing light olefin selectivity in the conversion of oxygenates using a small pore molecular sieve catalyst. The selectivity is increased by exposing a catalyst to a modifier before or during the conversion reaction. The modifier is a polynuclear aromatic having at least three interconnected ring structures, with each ring structure having at least 5 ring members. It is adsorbed onto the catalyst prior to or simultaneously with the introduction of feed.

U.S. Pat. No. 6,137,022 (Kuechler et al.) is to a process for increasing the selectivity of a reaction to convert oxygenates to olefins. The process involves contacting the oxygenate in a reaction zone containing 15 volume percent or less of a catalyst comprising SAPO molecular sieve, and maintaining conversion of the feedstock between 80% and 99% under conditions effective to convert 100% of the feedstock when the reaction zone contains at least 33 volume percent of the molecular sieve material. The process is considered to be beneficial in maximizing the production of ethylene and/or propylene, and to minimize the production of undesired products.

U.S. Pat. No. 6,436,869 (Searle et al.) is directed to a method of obtaining olefin product high in ethylene and/or propylene content, while reducing the amount of any one or more of $C_1$-$C_4$ paraffin by-products, and to reduce the amount of coke deposits on the catalyst during the reaction. The method is accomplished by providing a catalyst that comprises SAPO crystals, a binder comprising ALPO crystals, and nickel, cobalt and/or iron, wherein the catalyst does not contain significant amounts of amorphous binder.

U.S. Pat. No. 6,437,208 (Kuechler et al.) discloses a method for making olefin product from an oxygenate-containing feedstock. In the method, a SAPO molecular sieve catalyst is contacted with the oxygenate-containing feedstock in a reactor at an average catalyst feedstock exposure index of at least 1.0. The average catalyst feedstock exposure index is the total weight of oxygenate plus hydrocarbon fed to the reactor divided by the total weight of fresh and regenerated SAPO molecular sieve (i.e., excluding binder, inerts, etc., of the catalyst composition) sent to the reactor, both total weights measured over the same period of time. The method is shown to be effective in maintaining a high ethylene and propylene selectivity.

WO 01/62382 A2 (ExxonMobil Chemical Patents Inc.) discloses that selectivity to ethylene and propylene can be increased by pretreating a SAPO molecular sieve to form an integrated hydrocarbon co-catalyst within the framework of the molecular sieve prior to contacting with oxygenate feed. Acetone, methanol, propene, butene, pentene and hexene are given as examples of pretreatment compounds capable of forming an integrated hydrocarbon co-catalyst. The conditions for pretreatment include pretreating at a lower temperature relative to the reaction temperature. A preferred pretreatment vessel is an auxiliary fluidized bed reactor system associated with the oxygenate conversion reactor.

In spite of the recent technological advances in converting oxygenates to olefins, there remains a need to further increase the quantity of light olefins in the conversion product. In particular, there remains a need to increase product selectivity to ethylene and propylene, and particularly to ethylene. There also remains a need to reduce the amount of undesirable by-products in converting the oxygenates to olefins.

SUMMARY OF THE INVENTION

This invention provides methods or processes for converting oxygenates to olefins that show enhanced selectivity to light olefin (i.e., ethylene and/or propylene) product. The processes involve one or more of controlling the temperature of the reaction process, controlling the amount of coke on the molecular sieve, and applying a pretreatment composition to the molecular sieve.

In one embodiment, the reaction process of this invention involves a multi-stage process, whether requiring physically separate reactors or one reactor operating in continuous stages, that is maintained at a temperature to promote selectivity to light olefin. Preferably, each downstream stage of the process is at a temperature that is progressively lower than that of the previous stage.

In one aspect of the invention, there is provided a process for converting oxygenate to olefin. The process includes such steps as contacting the oxygenate with molecular sieve catalyst to form olefin in at least a two stage reactor system in series, and cooling between stages. The process has the benefit of increasing ethylene and/or propylene content of the olefin.

In another aspect of the invention, there is provided a process for converting oxygenate to olefin in a reactor system having at least two reaction stages in series. In this embodiment the oxygenate is contacted with molecular sieve catalyst to form the olefin, while cooling between at least two of the reaction stages.

In one embodiment of the invention, the molecular sieve catalyst is contacted in at least one of the reaction stages with $C_4+$ hydrocarbon to cool between stages.

In another embodiment, the molecular sieve is pretreated with a composition comprising at least one compound selected from the group consisting of $C_2$-$C_4$ aldehydes, $C_3$-$C_7$ ketones, $C_2$-$C_6$ ethers, $C_4$-$C_7$ olefins, and $C_1$-$C_5$ alcohols.

In another embodiment, the oxygenate is contacted with the molecular sieve catalyst in a first stage at a temperature of at least 480° C.

In yet another embodiment, cooling between each stage is from 5-50° C.

In another embodiment of the invention, the catalyst is introduced in the first stage at a coke content of not greater than 10 wt %, based on total weight of molecular sieve in the catalyst.

The invention further provides an embodiment in which the catalyst is introduced in the second stage at a coke content that is greater than that in the first stage.

Another embodiment provides that the catalyst is introduced in the second stage at a coke content of at least 4 wt %, based on total weight of molecular sieve in the catalyst. Preferably, the catalyst is introduced in the last stage at a coke content of not greater than 20 wt %, based on total weight of molecular sieve in the catalyst.

In a particular embodiment of the invention, the reaction system has a continuum of reaction stages in series. It is also preferred in one embodiment that cooling is continuous though each stage. It is further preferred that the coke content of the catalyst increases at each stage.

BRIEF DESCRIPTION OF THE DRAWING

Examples of various embodiments of the invention are shown in the attached Figures, wherein.

DETAILED DESCRIPTION OF THE INVENTION

I. Cooling to Increase Ethylene and/or Propylene Content

This invention is directed to a process for converting oxygenate to olefin product at an increased ethylene and/or propylene content compared to conventional systems. The increase in ethylene and/or propylene content of the produced olefin product is accomplished by using a reaction system that has at least two stages and incorporates cooling between stages. In other words, the reaction process is carried out such that the average reaction temperature at each stage is reduced at each subsequent stage.

There can be any number of stages used in the entire process, as long as there are at least two stages and the temperature of any subsequent stage is lower than that of the preceding stage. In general, the greater the number of stages, the less the temperature differential between stages. Preferably, the reaction system has a continuum of reaction stages in series. In addition, cooling is preferably continuous through each stage.

In one embodiment of the invention, the overall reactor system incorporates at least two stages, and up to N stages, in series, with N representing an integer greater than 1. In one embodiment, the reactor system has not greater than 10 stages in series. In another embodiment, the overall reactor system has not greater than 7 or 5 stages in series. In yet another embodiment, the overall reactor system has from 2 to 10 stages or from 2 to 7 stages or from 2 to 5 stages, each stage in series.

Each stage of the reactor system can contain the same or different catalyst, as long as there is progressive cooling from stage to stage. In one embodiment, cooling is continuous. In embodiments where cooling is continuous with feed flow, it can be considered that there are an infinite number of stages, since each stage will not necessarily be distinct. In embodiments where each stage is considered distinct, each distinct stage is preferably carried out in a separate reactor, or at least separate segments or compartments within the same reactor. More preferably, the distinct stages are carried out in series.

Conventional cooling means can be used to cool between reaction stages. For example, heat exchangers can be used between stages as cooling devices, the reactors themselves can be cooled by heating jackets, or various components can be added to the reaction process as desired to serve as heat sinks. As one example of the use of chemical compounds that can be used as heat sinks are $C_4+$ compositions. Such compositions contain at least 50% hydrocarbon compounds having at least 4 carbon atoms, based on total weight of the composition.

In one embodiment, the oxygenate feed is contacted with the molecular sieve catalyst in a first stage at a temperature of at least 480° C. Preferably, the oxygenate feed is contacted with the molecular sieve catalyst in a first stage at a temperature of from 500° C. to 600° C., more preferably from 510° C. to 560° C., and most preferably from 510° C. to 540° C.

In embodiments where cooling is not continuous between stages, cooling between each stage is preferably from 5° C. to 50° C., where each stage is in series. That is, the average temperature of any stage subsequent to the first stage is from 5° C. to 50° C. cooler than that of the previous stage in the series. In another embodiment, cooling between each stage is from 10° C. to 40° C., and in yet another embodiment, cooling between each stage is from 20° C. to 30° C.

In general, the degree of cooling between stages is inversely proportional to the amount of coke on the catalyst. That is, as the amount of coke increases, it is generally preferred to reduce the average temperature of each reaction stage proportionately. Although conversion generally decreases with increased coke content, selectivity to form ethylene and/or propylene from oxygenate feed can be increased over certain ranges of coke content. In addition, as the coke levels gradually rise, decreasing reaction temperature can also increase selectivity to form ethylene and/or propylene.

In one embodiment, the catalyst is introduced in the first stage at a relatively low coke content, preferably not greater than 10 wt %, based on total weight of the molecular sieve in the catalyst. Preferably, the catalyst is introduced in the first stage at a coke content of not greater than 8 wt %, more preferably not greater than 6 wt %, still more preferably not greater than 4 wt %, and most preferably not greater than 2 wt %, based on total weight of the molecular sieve in the catalyst.

As the catalyst is moved through subsequent stages, the coke content is generally increased. In one embodiment, the catalyst is introduced in each subsequent stage at a coke content of at least 1 wt % greater than that of the previous stage in the series, based on total weight of the molecular sieve in the catalyst. In another embodiment, the catalyst is introduced in each subsequent stage at a coke content of at least 2 wt %, 3 wt %, 4 wt % or 5 wt % greater than that of the previous stage in the series, based on total weight of the molecular sieve in the catalyst.

In one particular embodiment of the invention, the catalyst is introduced into the second stage at a coke content of at least 2 wt %, based on total weight of the molecular sieve in the catalyst. In yet another particular embodiment, the catalyst is introduced into the second stage at a coke content of at least 3 wt %, 4 wt % or 5 wt %, based on total weight of the molecular sieve in the catalyst.

In another embodiment of the invention, the catalyst is introduced in the last stage at a coke content of not greater than 20 wt %, based on total weight of the molecular sieve in the catalyst. In yet another embodiment, the catalyst is introduced in the last stage at a coke content of not greater than 18 wt % or 16 wt %, based on total weight of the molecular sieve in the catalyst.

II. Catlyst

Any catalyst capable of converting oxygenate to olefin can be used in this invention. Molecular sieve catalysts are preferred. Examples of such catalysts include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1-67, Elsevier Science, B.V., Amsterdam, Netherlands (2001).

Small, medium and large pore molecular sieves have from a 4-ring to a 12-ring or greater framework-type. In a preferred embodiment, the molecular sieves have 8-, 10- or 12-ring structures and/or an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161

489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. Pat. No. 6,743,747 (integrated hydrocarbon co-catalyst), PCT WO 01/64340 published Sep. 7, 2001(thorium containing molecular sieve), and R. Szostak, *Handbook of Molecular Sieves,* Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IIB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. Pat. No. 6,812,372 and PCT WO 98/15496, published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

In one embodiment, the molecular sieves used in the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A- 0 229,- 295), boron silicates (U.S. Pat. No.

4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve, in a preferred embodiment, is combined with one or more matrix materials. Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

III. Optional Catalyst Pretreatment

An optional pretreatment stage can be carried out if desired. An advantage in using a pretreatment stage is that a highly active catalyst can be pretreated to optimize coke content at a level that maximizes prime olefin (i.e., ethylene and propylene) selectivity. Examples of effective pretreatment compositions are those that contain at least one compound selected from the group consisting of $C_2$-$C_4$ aldehydes, $C_3$-$C_7$ ketones, $C_2$-$C_6$ ethers (particularly dimethyl ether), $C_4$-$C_7$ olefins, and $C_1$-$C_5$ alcohols.

In general, the temperature in the pretreatment zone is from about 150° C. to about 750° C. Preferably, the temperature in the pretreatment zone is from about 200° C. to about 750° C., more preferably from about 250° C. to about 750° C.

In one embodiment, the pretreatment temperature (i.e., the temperature in the pretreatment zone) is at least about the same as or greater than the temperature of the Stage 1 oxygenate reaction temperature. In a particular embodiment, the pretreatment temperature is greater than the oxygenate reaction temperature, particularly when $C_2$-$C_6$ ethers, more particularly dimethyl ether, or when $C_4$-$C_7$ olefins are used in the pretreatment composition. It is particularly preferred in such an embodiment that the temperature in the pretreatment zone is at least 10° C. higher than that in the oxygenate reaction zone. Preferably, the temperature in the pretreatment zone is at least 25° C., more preferably at least 50° C., and most preferably at least about 100° C. higher than that in the reaction zone. In one embodiment, the temperature in the pretreatment zone is at least 450° C. Preferably, the temperature in the pretreatment zone is at least 500° C., and most preferably at least 550° C.

In another particular embodiment, the pretreatment temperature is cooler than (i.e., less than) the oxygenate reaction temperature in Stage 1. Preferably, when $C_2$-$C_4$ aldehydes, especially acetaldehyde, are used in the pretreatment composition, the temperature in the pretreatment zone is at least 10° C. less than that in the oxygenate reaction zone. Preferably, the temperature in the pretreatment zone is at least 25° C., more preferably at least 50° C., and most preferably at least about 100° C. less than that in the reaction zone. In one embodiment, the temperature in the pretreatment zone is not greater than about 475° C. Preferably, the temperature in the pretreatment zone is not greater than about 425° C., and most preferably not greater than about 375° C. In another embodiment, the temperature in the pretreatment zone is from about 150° C. to about 475° C. Preferably, the temperature in the pretreatment zone is from about 200° C. to about 425° C., more preferably from about 250° C. to about 375° C.

Pretreatment of the molecular sieve is particularly effective on fresh, activated catalyst, or regenerated catalyst. Such catalyst is substantially low in total carbon content. As the fresh or regenerated catalyst contacts the pretreatment composition, the integrated hydrocarbon co-catalyst forms within the internal pore structure of the molecular sieve. In one embodiment, the molecular sieve that contacts the pretreatment composition to form the integrated hydrocarbon co-catalyst has a total carbon content of not greater than about 2 wt % prior to contact with the pretreatment composition. Preferably the molecular sieve catalyst that contacts the pretreatment composition has a total carbon content of not greater than about 1.5 wt %, more preferably not greater than about 1 wt %, and most preferably not greater than about 0.5 wt %, prior to contact with the pretreatment composition.

Following pretreatment, the molecular sieve contains the integrated hydrocarbon co-catalyst, which is a benzene type compound, within the various cages of the internal pore structure. In addition to using SSNMR to determine appropriate pretreatment of the molecular sieve, an additional embodiment involves measuring hydrocarbon content of the molecular sieve that has contacted the pretreatment composition. In one embodiment, the molecular sieve containing the integrated hydrocarbon co-catalyst has a hydrocarbon content of at least 0.1 wt %, preferably at least 1 wt %, more preferably at least about 5 wt %, and most preferably at least about 10 wt %, based on total weight of the molecular sieve, which excludes non-molecular sieve components such as binder, matrix, etc., which are optionally present in a catalyst composition.

In general, the molecular sieve that is being pretreated contacts the pretreatment composition in the pretreatment zone at a weight hourly space velocity (WHSV) that is lower than the WHSV of the molecular sieve contacting the oxygenate in the oxygenate reaction zone. In one embodiment, the molecular sieve contacts the pretreatment composition at a WHSV that is at least 5 $hr^{-1}$ lower than that of the molecular sieve contacting the oxygenate in the oxygenate reaction zone. Preferably, the molecular sieve contacts the pretreatment composition at a WHSV that is at least about 10 $hr^{-1}$, more preferably at least about 15 $hr^{-1}$ lower than that of the molecular sieve contacting the oxygenate in the oxygenate reaction zone.

In one embodiment, the molecular sieve and the pretreatment composition contact one another in a pretreatment zone at a WHSV of from about 5 $hr^{-1}$ to about 200 $hr^{-1}$. WHSVs in the lower range are preferred, particularly from about 10 $hr^{-1}$ to about 100 $hr^{-1}$, and more particularly from about 20 $hr^{-1}$ to about 80 $hr^{-1}$.

The pretreatment zone can be contained in a separate pretreatment zone or within a reactor vessel where the Stage 1 conversion of oxygenate to olefin takes place. In one embodiment, a separate pretreatment vessel is used. In a particular embodiment, the pretreatment vessel is an auxiliary fluidized bed reactor associated with the Stage 1 conversion reactor. The auxiliary reactor is capable of continuously receiving catalyst from the regenerator and subsequently supplying pretreated catalyst to Stage 1 of the oxygenate conversion reactor system.

In another embodiment, pretreatment is carried out within the same vessel where the Stage 1 catalytic conversion of oxygenate to olefin product takes place. Preferably, two separate temperature zones are maintained to get proper introduction of hydrocarbon and formation of the integrated hydrocarbon co-catalyst. In one aspect, the molecular sieve to be pretreated is introduced into one zone along with the pretreatment composition to form the integrated hydrocarbon co-catalyst. Then, the pretreated molecular sieve containing the integrated hydrocarbon co-catalyst is sent to Stage 1 and contacted with oxygenate to convert the oxygenate to olefin product. Operating conditions in the different zones and/or stages are controlled for pretreatment and oxygenate reaction conditions. One or more of the zones or stages optionally includes heating or cooling equipment such as heat exchangers, steam coils, and cooling coils. In one embodiment, the pretreatment zone includes cooling equipment.

IV. Overall Operating Conditions

According to the reaction process of this invention, oxygenate is contacted with olefin forming catalyst to form an olefin product, particularly ethylene and propylene. The process for converting the oxygenate feedstock is, preferably, a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

One preferred reactor type is a riser reactor. These types of reactors are generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one embodiment of the invention, a fluidized bed process or high velocity fluidized bed process includes a reactor system, catalyst separation system, and a regeneration system. The reactor system preferably is a fluid bed reactor system. In one embodiment, the fluid bed reactor system has a first reaction zone within one or more riser reactors, and a second reaction zone within at least one catalyst separation vessel, preferably comprising one or more cyclones. In one embodiment, one or more riser reactors and catalyst separation vessel is contained within a single reactor vessel.

An oxygenate stream, preferably containing one or more oxygenates, and optionally one or more diluents, is fed to a fluid bed reactor in which a molecular sieve catalyst composition is introduced. In one embodiment, the molecular sieve catalyst composition is contacted with a liquid or gas, or combination thereof, prior to being introduced to the riser reactor. Preferably, the liquid is water or methanol, and the gas is an inert gas such as nitrogen.

In one embodiment of the invention, the temperature of the regenerator is indirectly controlled by controlling the amount of heat generated in the reactor. One example of controlling the amount of heat generated is by introducing at least a portion of the oxygenate stream into the reactor in liquid form. The greater the liquid content, the less heat generated, since the exothermic heat of reaction of oxygenate conversion is partially absorbed by the endothermic heat of vaporization of the liquid portion of the feed.

In another embodiment, the amount of oxygenate stream that is fed to a reactor system in liquid form is from about 0.1 weight percent to about 85 weight percent, based on the total weight of the oxygenate stream, including any diluent contained therein. Preferably the amount of the oxygenate stream that is fed to the reactor system in liquid form is from about 1 weight percent to about 75 weight percent, more preferably from about 5 weight percent to about 65 weight percent, based on the total weight of the oxygenate stream, including any diluent contained therein.

The liquid and vapor portion of the feed may be the same composition, or may contain varying proportions of the same or different oxygenates and same or different diluents. One particularly effective liquid diluent is water, due to its relatively high heat of vaporization. Other useful diluents are described above. Proper selection of the temperature and pressure of any appropriate oxygenate and/or diluent being fed to the reactor will ensure at least a portion is in the liquid phase as it enters the reactor and/or comes into contact with the catalyst or a vapor portion of the feed and/or diluent.

Optionally, the liquid fraction of the oxygenate stream is split into portions and introduced into the reactor at a multiplicity of locations along its length. This can be done with the oxygenate feed, the diluent, or both. Preferably, this is done with the diluent portion of the feed. Another option is to provide a nozzle which introduces the total liquid fraction of the feed into the inlet zone or reactor in a manner such that the nozzle forms liquid droplets of an appropriate size distribution which, when entrained with the gas and solids introduced to the inlet zone or reactor, vaporize gradually along the length of the reactor. Either of these arrangements or a combination thereof may be used to better control the amount of heat generated. The means of introducing a multiplicity of liquid feed points in a reactor or designing a liquid feed nozzle to control droplet size distribution is well known in the art and is not discussed here.

This invention involves maintaining the reaction process, especially a multi-stage reaction system, at a temperature in which a subsequent stage is cooler (i.e., kept at a lower temperature) than the previous stage. However, it is preferred that the overall average reaction temperature employed in the conversion process, specifically within each stage of the multi-stage reaction system, is of from about 250° C. to about 800° C. Preferably the average reaction temperature is from about 250° C. to about 750° C.; more preferably, from about 300° C. to about 650° C.; yet more preferably from about 350° C. to about 600° C.; and most preferably from about 400° C. to about 500° C.

The pressure employed in the conversion process, specifically within any one or more reaction stages of the reaction system, is not critical. The reaction pressure is based on the partial pressure of the feedstock exclusive of any diluent therein. Typically the reaction pressure employed in the overall process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within any one reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV in any one or more reaction stages ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within any one or more reaction stages is preferably sufficient to fluidize the molecular sieve catalyst composition within a reaction zone of the reactor. The SGV in the process, particularly within any one or more reaction stages, is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec.

According to one embodiment, the conversion of oxygenate, particularly methanol, in the overall reaction process, is from 90 wt % to 98 wt %. According to another embodiment the conversion of oxygenate is from 92 wt % to 98 wt %, preferably from 94 wt % to 98 wt %.

According to another embodiment, the conversion of oxygenate is above 98 wt % to less than 100 wt %. According to another embodiment, the conversion of oxygenate is from 98.1 wt % to less than 100 wt %; preferably from 98.2 wt % to 99.8 wt %. According to another embodiment, the conversion of oxygenate is from 98.2 wt % to less than 99.5 wt %; preferably from 98.2 wt % to 99 wt %.

V. Olefin Product Recovery and Use

In one embodiment, olefin product and other gases are withdrawn from the reactor system and are passed through a recovery system. Any conventional recovery system, technique and/or sequence useful in separating olefin(s) and purifying olefin(s) from other gaseous components can be used in this invention. Examples of recovery systems include one or more or a combination of various separation, fractionation and/or distillation towers, columns, and splitters, and other associated equipment; for example, various condensers, heat exchangers, refrigeration systems or chill trains, compressors, knock-out drums or pots, pumps, and the like.

Non-limiting examples of distillation towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene ($C_2$) splitter, propylene ($C_3$) splitter, butene ($C_4$) splitter, and the like.

Various recovery systems useful for recovering predominately olefin(s), preferably prime or light olefin(s) such as ethylene, propylene and/or butene are described in U.S. Pat. Nos. 5,960,643, 5,019,143, 5,452,581 and 5,082,481, 5,672,197, 6,069,288, 5,904,880, 5,927,063, and 6,121,504, 6,121,503, and 6,293,998, which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249-271 and 894-899, which is herein incorporated by reference. Purification systems are also described in for example, U.S. Pat. Nos. 6,271,428, 6,293,999, and U.S. patent application Ser. No. 09/689,363 filed Oct. 20, 2000, which are herein incorporated by reference.

The ethylene and propylene streams produced and recovered according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4+$ olefins, particularly butylene, separated according to this invention. The olefins separated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_2$-$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butylene in particular, are particularly suited for the manufacture of aldehydes, acids, alcohols, esters made from $C_5$-$C_{13}$ mono carboxylic acids and $C_5$-$C_{13}$ mono alcohols and linear alpha olefins.

V. EXAMPLES

Experimental Details

Experiments were performed with the use of a microflow reactor. Formulated SAPO-34 catalyst, which contained 45 wt % SAPO-34 molecular sieve with the rest being binder, clay and other matrix materials, was mixed with 1 g of siliconcarbide. The mixture was loaded into a reactor made of ¼" siliconsteel tubing. The reactor temperature was increased to the desired reaction temperature while the catalyst was held under He flow (46 ml/min) for ca. 30 to 40 min. for the temperature to stabilize. The temperature rise observed in the experiments was 5° C. or less as a result of reaction exotherm from methanol conversion. The flowrate of methanol was kept essentially constant at 80 μl/min. The amount of catalyst used was ca. 84 mg of formulated catalyst.

The reactor effluent was sampled in a 15-loop sampling valve to obtain the gas phase selectivity data. The collected effluent samples were analyzed by on-line gas chromatography (Hewlett Packard 6890) equipped with a flame ionization detector. The chromatographic column used was a Q-column.

The selectivity data, reported in Examples 1-3, were weighed averages calculated based on the following formula, $x_1*y_1+(x_2-x_1)*y_2+(x_3-x_2)*(y_2+y_3)/2+(x_4-x_3)*(y_3+y_4)/2+\ldots$, where $x_i$ and $y_i$ are yields for products from the methanol to olefin (MTO) conversion reactions and g methanol fed/g sieve, respectively, as measured by gas chromatography (GC) at different time-on-stream. Methanol converted at less than ca. 10% conversions was not counted in the calculations.

Coke selectivity data, see Example 2, was derived using hydrogen-carbon balance assuming that coke is the only hydrogen-deficient species while methane, ethane and propane are the only hydrogen-rich species. As a result, the following equation can be derived based on the H—C balance:

$$\text{Coke selectivity} = (12+H/C)*(S_{methane}/8+S_{ethane}/15+S_{propane}/22)/(2-H/C)$$

H/C is the ratio of hydrogen to carbon of the coke derived from the methanol conversion. The ratio is a function of amount of coke on catalyst. The following empirical equation was used to calculate the H/C ratio, $$H/C = 1117 * \exp(-87 * COS) / (1 + 756 * \exp(-87 * COS))$$

where COS is the amount of coke on the total weight of SAPO-34 sieve of the catalyst at different time-on-stream.

Example 1

Figure 1:
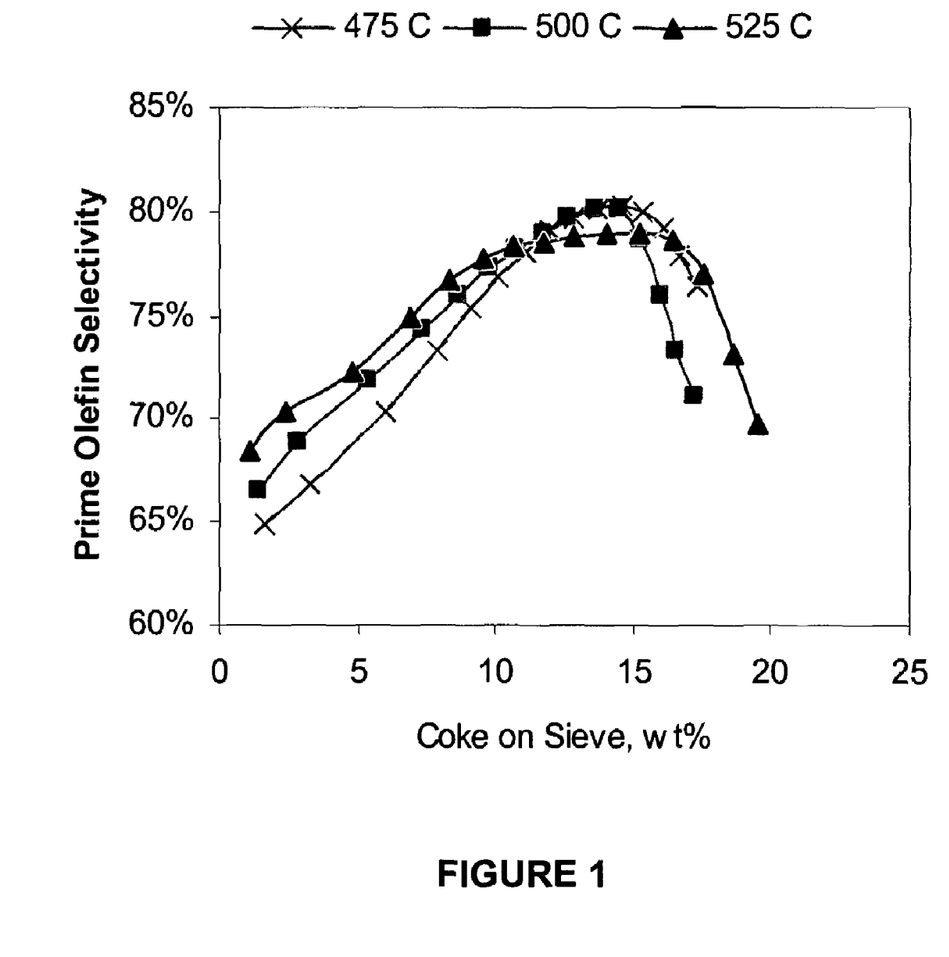
FIG. 1 is a graph showing one example of prime olefin selectivity of one particular catalyst as a function of coke content of the molecular sieve in the catalyst.

FIG. 1 shows prime olefin selectivity (POS, or the sum of ethylene and propene selectivity) as a function of coke on sieve for a SAPO-34 catalyst measured at 475° C., 500° C. and 525° C., respectively. FIG. 1 shows that prime olefin selectivity is higher at increased reaction temperatures when coke on sieve level is less than about 11 wt %. However, prime olefins selectivity is higher at reduced reaction temperature when coke on sieve level is between about 12 to 16 wt %.

Example 2

Table 1 shows prime olefin selectivity increase (ΔPOS) estimated by combining superior POS at higher temperatures (500 C and 525 C) averaged up to the indicated coke on sieve with performance at 475 C from the indicated coke on sieve to the end-of-run coke on sieve. It was assumed that coke produced at different MTO reaction temperatures (from 475 C to 525 C) was identical.

TABLE 1

| Coke on Sieve | ΔPOS | | |
|---|---|---|---|
| (wt. %) | 475° C. | 500° C. | 525° C. |
| 0 | 0.00% | 0.12% | 0.50% |
| 3 | 0.00% | 0.23% | 0.47% |
| 5 | 0.00% | 0.39% | 0.75% |
| 8 | 0.00% | 0.87% | 1.52% |

The data in Table 1 show the improvement in prime olefin selectivity (POS) when the methanol to olefin reactions were carried out at progressively lower temperatures. In general, the higher temperatures and higher coke levels show a greater effect on ΔPOS.

Example 3

Figure 2:
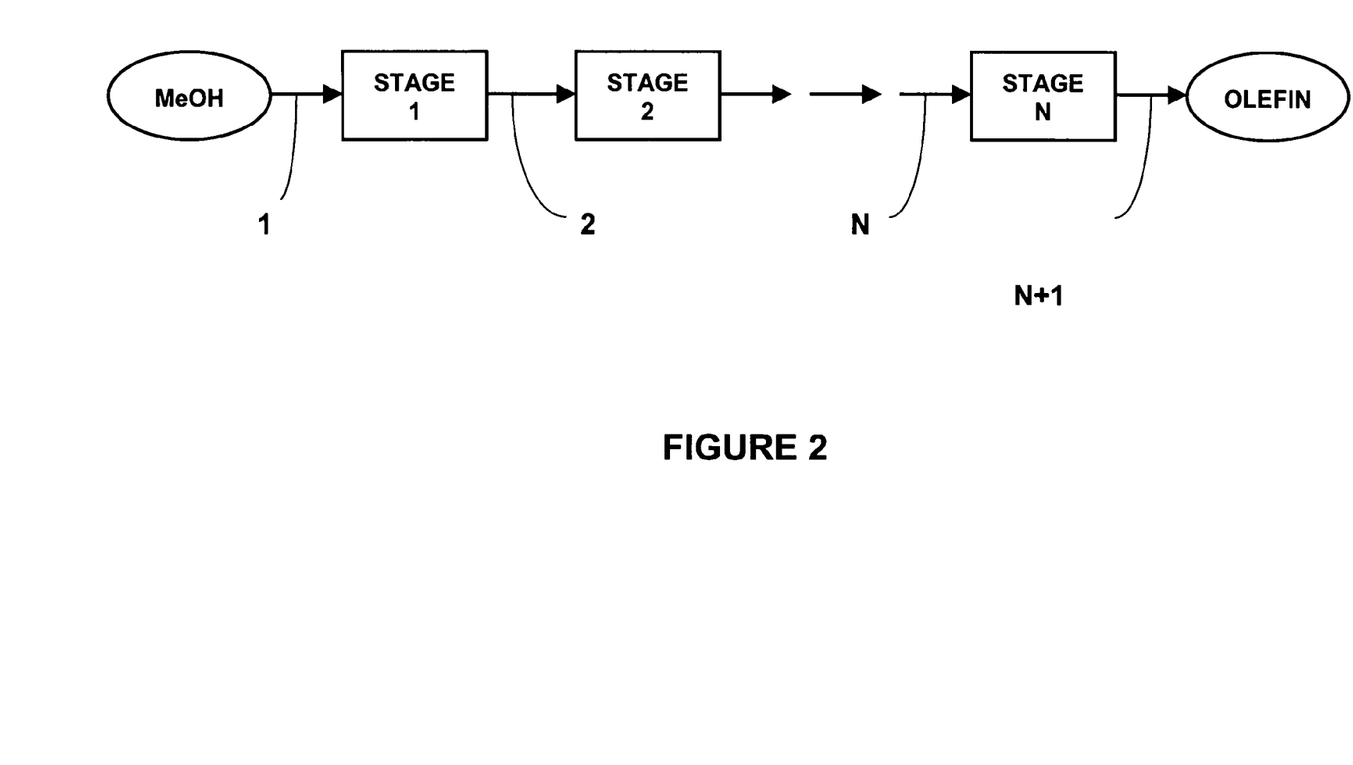
FIG. 2 is a flow diagram showing an example of a multi-stage reaction system that can be used in this invention.

An example of the process of this invention is shown in FIG. 2, which depicts the reaction stages of the reaction system as a simple flow diagram. According to the embodiment in FIG. 2, methanol is used as the oxygenate, and the methanol is input into Stage 1 of a reactor system by way of a line 1. In stage 1, the methanol is contacted with a molecular sieve catalyst and at least a portion of the methanol is converted to olefin. As the conversion is carried out, a coke layer builds on the catalyst, and as the coke layer builds to the desired level, the conversion is more selective toward ethylene and/or propylene. At a predetermined point, such as at a predetermined level of coke or a predetermined level of temperature rise, the catalyst, product and unreacted feed is passed from Stage 1 through a line 2, cooled, and the reaction continued in a Stage 2. At another predetermined point, the catalyst, product and unreacted feed can be passed to any number of other stages as desired through N number of lines to a final Stage N with appropriate cooling between each stage, where N represents an integer greater than 2. Finally, olefin product rich in ethylene and/or propylene is recovered from the final Stage N through a line N+1.

Having now fully described this invention, it will be appreciated by those skilled in the art that the invention can be performed within a wide range of parameters, without departing from the spirit and scope of the invention.

We claim:

1. A process for converting oxygenate to olefin, comprising:
   a) contacting the oxygenate with molecular sieve catalyst to form olefin in at least a two stage reactor system in series, wherein the catalyst that is introduced into the second stage has a coke content of at least 2 wt %, based on total weight of the molecular sieve in the catalyst, and a coke content that is greater than that of the first stage, and the catalyst that is introduced in the last stage has a coke content of not greater than 20 wt %, based on total weigh of the molecular sieve in the catalyst; and
   b) cooling between stages such that any subsequent reactor stage has a temperature that is lower than that of the preceding reactor stage, thereby increasing ethylene and/or propylene content of the olefin.

2. The process of claim 1, wherein the molecular sieve catalyst is contacted in at least one of the reaction stages with $C_4+$ hydrocarbon to cool between stages.

3. The process of claim 1, wherein the molecular sieve is pretreated with a composition comprising at least one compound selected from the group consisting of $C_2$-$C_4$ aldehydes, $C_3$-$C_7$ ketones, $C_2$-$C_6$ ethers, $C_4$-$C_7$ olefins, and $C_1$-$C_5$ alcohols.

4. The process of claim 1, wherein the oxygenate is contacted with the molecular sieve catalyst in a first stage at a temperature of at least 480° C.

5. The process of claim 1, wherein cooling between each stage is from 5-50° C.

6. The process of claim 1, wherein the catalyst is introduced in the first stage at a coke content of not greater than 10 wt %, based on total weight of molecular sieve in the catalyst.

7. The process of claim 1, wherein the catalyst is introduced in the second stage at a coke content of at least 4 wt %, based on total weight of molecular sieve in the catalyst.

8. The process of claim 1, wherein the reaction system has a continuum of reaction stages in series.

9. The process of claim 1, wherein cooling is continuous though each stage.

10. The process of claim 1, wherein coke content of the catalyst increases at each stage.

11. A process for converting oxygenate to olefin in a reactor system having at least two reaction stages in series, comprising contacting the oxygenate with molecular sieve catalyst to form the olefin, wherein the catalyst that is introduced into the second stage has a coke content of at least 2 wt %, based on total weight of the molecular sieve in the catalyst, and a coke content that is greater than that of the first stage, and the catalyst that is introduced in the last stage has a coke content of not greater than 20 wt %, based on total weigh of the molecular sieve in the catalyst, while cooling between at least two of the reaction stages such that any subsequent reactor stage has a temperature that is lower than that of the preceding reactor stage.

12. The process of claim 11, wherein the molecular sieve catalyst is contacted in at least one of the reaction stages with $C_4+$ hydrocarbon to cool between stages.

13. The process of claim 11, wherein the molecular sieve is pretreated with a composition comprising at least one compound selected from the group consisting of $C_2$-$C_4$ aldehydes, $C_3$-$C_7$ ketones, $C_2$-$C_6$ ethers, $C_4$-$C_7$ olefins, and $C_1$-$C_5$ alcohols.

14. The process of claim 11, wherein the oxygenate is contacted with the molecular sieve catalyst in a first stage at a temperature of at least 480° C.

15. The process of claim 11, wherein cooling between each stage is from 5-50° C.

16. The process of claim 11, wherein the catalyst is introduced in the first stage at a coke content of not greater than 10 wt %, based on total weight of molecular sieve in the catalyst.

17. The process of claim 11, wherein the catalyst is introduced in the second stage at a coke content of at least 4 wt %, based on total weight of molecular sieve in the catalyst.

18. The process of claim 11, wherein the reaction system has a continuum of reaction stages in series.

19. The process of claim 11, wherein cooling is continuous though each stage.

20. The process of claim 11, wherein coke content of the catalyst increases at each stage.

* * * * *